United States Patent
Tuma et al.

(10) Patent No.: US 8,688,409 B2
(45) Date of Patent: Apr. 1, 2014

(54) METHOD FOR DETERMINING AN ARRANGEMENT OF MEASUREMENT POINTS ON AN ANATOMICAL STRUCTURE

(75) Inventors: Gregor Tuma, München (DE); Frank Grünschläger, Feldkirchen (DE); Martin Adamski, München (DE); Andreas Oschinski, München (DE)

(73) Assignee: Brainlab AG, Feldkirchen (DE)

( * ) Notice: Subject to any disclaimer, the term of this patent is extended or adjusted under 35 U.S.C. 154(b) by 621 days.

(21) Appl. No.: 12/697,383

(22) Filed: Feb. 1, 2010

(65) Prior Publication Data

US 2010/0198564 A1 Aug. 5, 2010

Related U.S. Application Data

(60) Provisional application No. 61/168,013, filed on Apr. 9, 2009.

(30) Foreign Application Priority Data

Jan. 30, 2009 (EP) ...................... 09151686

(51) Int. Cl.
*G06F 17/50* (2006.01)
(52) U.S. Cl.
USPC ................. 703/1; 703/11; 434/262; 434/275; 434/267; 434/274; 600/410; 600/414; 600/411; 382/131; 382/154; 382/128
(58) Field of Classification Search
USPC ........... 600/411, 300, 410; 382/128, 131, 132
See application file for complete search history.

(56) References Cited

U.S. PATENT DOCUMENTS 5,377,011 A 12/1994 Koch
2007/0249967 A1 10/2007 Buly et al.

OTHER PUBLICATIONS

Nobuhiko Sugano et al. Accuracy Evaluation of Surface-Based Registration Methods in a Computer Navigation System for Hip Surgery Performed Through a Posterolateral Approach Computer Aided Surgery, 6:195-203, 2001.*
Dean C. Barratt et al. Self-Calibrating 3D-Ultrasound-Base Bone Registration for Minimally Invasive Orthopedic Surgery IEEE Transactions on Medical Imaging, vol. 25, No. 3, Mar. 2006.*
Barratt et al. Instantiation and registration of statistical shape models of the femur and pelvis using 3D ultrasound imaging Medical Image Analysis vol. 12, Issue 3, Jun. 2008, pp. 358-374.*
Zhang et al., "From Range Data to Animated Anatomy-Based Faces: A Model Adaptation Method", 3-D Imaging and Modeling, 2005, pp. 343-350.
F.I. Parke et al., "Computer Facial Animation", pp. 83-84, 1996 (previously submitted on Jul. 23, 2010).

* cited by examiner

*Primary Examiner* — Omar Fernandez Rivas
*Assistant Examiner* — Cuong Luu
(74) *Attorney, Agent, or Firm* — Tucker Ellis LLP (57) ABSTRACT

A method for determining arrangement data which represents an arrangement of measurement points on an anatomical structure of a patient, wherein the arrangement data is individually determined for different regions of the anatomical structure.

17 Claims, 4 Drawing Sheets

METHOD FOR DETERMINING AN ARRANGEMENT OF MEASUREMENT POINTS ON AN ANATOMICAL STRUCTURE

RELATED APPLICATION DATA

This application claims the priority of U.S. Provisional Application No. 61/168,013, filed on Apr. 9, 2009, which is hereby incorporated in its entirety by reference.

FIELD OF THE INVENTION

The present invention relates to a method and device for determining an arrangement of measurement points on an anatomical structure of a patient.

BACKGROUND OF THE INVENTION

Morphing a generic model of an anatomical model structure, for example a bone, onto the anatomical structure is known in medical applications. An anatomical structure is a structure of a body, for example a bone or an organ, of a patient. The generic model of the anatomical structure serves to (approximately) describe and/or reproduce the anatomical structure.

As input values for the actual morphing process, measurement points on the surface of the anatomical structure are scanned by means of a scanning method, for example using a pointer. In this way, measurement point data has been generated which in particular represent the location of the measurement points, preferably in three dimensions. The generic model is then altered such that it corresponds to the scanned measurement points. The model is usually a grid network model comprising a multitude of grid points, which is also referred to as a point distribution model (PDM).

The model is in particular represented by model data, wherein the model data preferably includes the two-dimensional or three-dimensional locations of the grid points. The model is for example a statistical model obtained from surveying a multitude of identical structures. During morphing, the position of the grid points relative to each other is adapted such that the model, in particular in the form of the model data, matches the measurement points, i.e. simulates the anatomical structure, as closely as possible. This process, which is also referred to as matching, is known in the prior art.

SUMMARY OF THE INVENTION

Depending on the type of anatomical structure, it is necessary to scan up to several hundred measurement points. This results in a considerable expenditure of time in order to scan the anatomical structure. It is the object of the present invention to reduce the time necessary for scanning.

This object is solved by: a method for determining arrangement data which represents an arrangement of measurement points on an anatomical structure of a patient, wherein the arrangement data is individually determined for different regions of the anatomical structure; a software program which, when it is run on a computer or loaded onto a computer, performs the method steps of the method as described above; a computer-readable medium on which the software program as described above is stored; and a device for determining arrangement data which represents an arrangement of measurement points on an anatomical structure, said device comprising a computer which is designed to perform the method as described above. The invention also relates to a method for morphing a generic model of an anatomical structure onto an anatomical structure of a patient on the basis of measurement point data which represents the anatomical structure at measurement points, wherein arrangement data which represents the arrangement of the measurement points is determined on the basis of a method as described above. Advantageous embodiments may be gathered from the dependent claims.

In accordance with the invention, the arrangement data which represents the arrangement of the measurement points is individually determined for different regions of the anatomical structure. This results in the ideal arrangement of the measurement points for each region, wherein the term "arrangement" includes in particular the number of and/or distance between the measurement points and/or the number of measurement points per unit area (for example $cm^2$) of the scanned area. The determined arrangement data is preferably output as arrangement signals which include arrangement information, in particular by a computer. The arrangement data is the entirety of the arrangement data of all the (relevant) regions.

The measurement point data is for example ascertained by a scanning method and then provided to the computer via an interface for processing. The arrangement data is provided to the scanning method. The method for determining the arrangement data and the scanning method are usually methods which can be performed separately.

In the previous scanning methods, it is usual to scan the measurement points in a static point screen, wherein regions of the anatomical structure which may be non-critical are scanned too finely and critical regions of the anatomical structure are scanned too roughly. By taking into account arrangement data, as is preferred, it is possible to respectively scan different regions of the anatomical structure at the optimum number of points and/or the optimum point density (i.e. number per unit area) and/or at the optimum point distance and thus prevent points which are not needed from being scanned.

The method in accordance with the invention is in particular a data processing method. The data processing method is preferably performed using technical means, in particular a computer. The computer in particular comprises a processor and in particular a memory in order to process the data, in particular electronically. The calculating and/or determining steps described are in particular performed by a computer. Steps of defining for example regions or values are in particular steps of is determining data within the framework of the technical data processing method, in particular within the framework of a program. Modifying steps in particular represent modifying the data by means of the computer.

The measurement points are preferably described by measurement point data. The arrangement data in particular describes the number of measurement points and/or the distance between the measurement points. The determining and ascertaining steps are preferably performed by a computer, in particular automatically. To this end, the computer can also perform calculations. The arrangement data is in particular determined with the aid of a computer. The measurement point data and arrangement data mentioned is preferably provided. Anatomical structure data which describes the anatomical structure is also preferably provided.

Where data, regions, ranges or images are "provided", this means that they are ready for use by the method in accordance with the invention. The data, regions, ranges or images can achieve this state of being "provided" by for example being detected or captured (for example by analysis apparatuses) or by being input (for example via interfaces). The data can also have this state by being stored in a memory (for example a ROM, CD and/or hard drive) and thus provided for use within the framework of the method in accordance with the invention.

In one embodiment of the invention, the computer determines the arrangement data on the basis of the complexity of the respective region and/or at least one adjacent region. The higher the complexity of the region, the greater the number of measurement points and/or the smaller the distance between the measurement points which is (automatically) selected in this region, wherein the complexities are determined on the basis of the anatomical structure, the generic model or a combination of the two.

Complexity data is then preferably used which describes the complexity of at least one region. The complexity data is for example data which represents values.

Any scale can be used for categorizing the complexity, for example a scale comprising values from 1 to 10, 1 to 20, 1 to 50 or 1 to 100, wherein the value 1 respectively signifies the smallest complexity on the scale. Any other quantification of the complexity is also possible.

In one embodiment of the invention, regions of the generic model of the anatomical structure which correspond to the regions of the anatomical structure are determined, and the complexity of a region of the anatomical structure is ascertained is from the complexity of the corresponding region of the generic model. The complexity of the corresponding regions of the anatomical structure and the complexity of the generic model are advantageously equated.

The information on the basis of which the arrangement of the measurement points is determined is thus not or not exclusively obtained from the anatomical structure, but rather (also) from the generic model. The intermediate step concerning the complexity of the region of the anatomical structure can be omitted, such that the arrangement data in a region of the anatomical structure is directly ascertained from the complexity of the corresponding region of the generic model.

Each grid point of the generic model is for example assigned a complexity, and the complexity of a region of the generic model is ascertained from the complexity of the grid points in this region. Preferably, the greatest complexity of all the grid points in the respective region of the generic model is determined as the complexity of the region of the anatomical structure. Alternatively, the complexity of the region of the generic model is ascertained as the average value of the complexities of all the grid points in the region. Averaging is non-weighted or weighted—for example, higher complexities are assigned a higher weighting factor than lower complexities when averaging.

In another example, the complexity of a region of the generic model is determined from the density of the grid points of the generic model in this region. If the density of the grid points of the generic model is high, then the complexity of the region of the generic model and therefore of the anatomical structure is also high, and vice versa. This is substantiated by the fact that the grid network of the generic model is usually denser in regions having a complex surface profile of the anatomical structure than in regions having a lower surface complexity. In this case, the number of grid points in a region of the generic model, preferably in relation to the area of the region, can be defined as a measure of the complexity of the region.

In accordance with another embodiment, the complexity of a region of the generic model is ascertained on the basis of the variance of the scanning values, averaged with respect to the generic model, of the structures in this region. This is an expedient criterion if the generic model is a statistical model. A statistical model is ascertained by averaging the scanning values of a multitude of homogenous surveyed structures, i.e. when forming the model, a multitude of structures of the same type—for example in the order of 50 to 200—are scanned and averaged to form the model. If all the surveyed structures in a region are identical or highly similar, this region of the generic model is assigned a low complexity. If the surveyed structures in this region are significantly different, this region is assigned a high complexity. Particular variance values of the generic model are for example assigned particular complexity values in a stored reference table, and the complexity values can be automatically determined by the computer, on the basis of data concerning the generic model, with the aid of the reference table.

The generic model is optionally adapted to the anatomical structure of the patient on the basis of pre-registration data which represents landmarks of the anatomical structure of the patient, and the complexity of a region of the anatomical structure is ascertained from the complexity of the corresponding region of the generic model adapted in this way. Using these method steps, the generic model is initially adapted roughly to the anatomical structure. This is advantageous, since an anatomical structure can exhibit a different size and/or shape depending on the patient, wherein the generic model is also optionally oriented such that its virtual position matches the position of the anatomical structure. Assigning a scanned region to the corresponding point of the generic model is thus simplified.

A landmark is a defined, characteristic point of an anatomical structure which is always identical or recurs with a high degree of similarity in the homogenous anatomical structure of a number of patients. Typical landmarks are for example the epicondyles of a femoral bone or the tips of the transverse processes and/or dorsal process of a vertebra.

In another embodiment, the arrangement data of a region is determined from an image of the anatomical structure. The image is for example an x-ray image, a CT recording, an MRT recording or other image such as is generated by an imaging method. The image is analyzed in order to ascertain which region needs to be more precisely or less precisely scanned and to correspondingly determine the arrangement data and/or complexity of the region.

The image is analyzed either by an operator or automatically. When evaluated automatically, the image is for example compared with a corresponding image resulting from the generic model. Obtaining a two-dimensional image from three-dimensional data, such as the generic model, is known as digitally reconstructed radiography (DRR). The complexity of the region and/or the arrangement data in this region is/are determined on the basis of the deviation between the two images in this region. Alternatively or additionally, the complexity of the region of the anatomical structure is obtained from the information density of the image in this region. The information density follows for example from the energy density or the frequency spectrum, in particular the proportion of high-frequency image portions in the image and/or region of the image.

The invention also relates to a method for morphing a generic model of an anatomical structure onto an anatomical structure of a patient on the basis of measurement point data, wherein the arrangement of the measurement points is determined on the basis of a method as described above. This not only reduces the time necessary for scanning but also the duration of the morphing step, since potentially fewer measurement points have to be taken into account in said step. The measurement point data describes the measurement points and therefore the surface of the anatomical structure at the measurement points.

When being morphed, the generic model is optionally adapted to the arrangement data, for example by altering the number and/or distribution of the grid points of the generic model as a whole or in a region. This means structurally altering the generic model, for example on the basis of the measurement point data. If, for example, a region of the model cannot be morphed onto the position of the scanned measurement points, as described by the measurement point data, within a maximum permissible deviation, for example because this region of the anatomical structure exhibits more complex surface characteristics than can be imaged by the model, then the model is supplemented by additional grid points.

The invention also relates to a device for determining arrangement data which represents an arrangement of measurement points on an anatomical structure, said device comprising a computer which is designed to perform the method as described above, i.e. the computer determines the arrangement data for each region. To this end, the generic model is stored in the computer or in a memory unit which the computer can access.

The device preferably also comprises a scanning device for scanning measurement points on the surface of the anatomical structure. The device therefore serves not only to determine the arrangement data but also to perform the scanning method. The scanning device is for example a pointer. The pointer is for example provided with a marker device or a reference star, the spatial position (i.e. the spatial location and/or alignment) of which is detected. The location of the tip of the pointer can be calculated from the position of the marker device and/or reference star and the position of the tip of the pointer relative to the marker device and/or reference star, and used as a measurement point of the surface of the anatomical structure.

Individual points on the surface of the anatomical structure are for example scanned using the tip of the pointer. Alternatively, the tip is moved over the surface and the location of the tip of the pointer is recorded as a measurement point at predetermined chronological or spatial intervals.

It is the function of a marker to be detected by a marker detection device (for example, a camera or an ultrasound receiver), such that its spatial position (i.e. its spatial location and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A "reference star" designates a device to which a number of markers, advantageously three markers, are attached, wherein the markers are attached stationary and advantageously detachably to the reference star, such that a known (advantageously fixed) position of the markers relative to each other is created. The position of the markers relative to each other can be individually different for each reference star used within the framework of a surgical navigation method, in order to enable the corresponding reference star to be identified by a surgical navigation system on the basis of the position of the markers relative to each other. The objects (for example, instruments and/or body parts) to which the reference star is attached can therefore also then be identified and/or distinguished from each other. In a surgical navigation method, the reference star serves to attach a plurality of markers to an object (for example, a bone or a medical instrument), in order to be able to detect the spatial position of the object (i.e. its location and/or alignment). Such a reference star in particular includes a way of being attached to the object (for example, a clamp and/or a thread) and/or a holding element which ensures a distance between the markers and the object (in particular in order to aid the visibility of the markers to a marker detection device) and/or marker holders which are mechanically connected to the holding element and to which the markers can be attached. Where it is clear from the context, the term "reference star" can also refer to a reference star with at least one marker attached to it. Such a system consisting of a reference star and at least one marker can also be referred to as a marker star.

The invention also relates to a software program which, when it is run on a computer or loaded onto a computer, performs the method steps according to one of the methods described above, and to a computer-readable medium on which such a software program is stored.

Computer program elements within the framework of the invention can be embodied by hardware and/or software (this also includes firmware, resident software, micro-code, etc.). Computer program elements within the framework of the invention can take the form of a computer program product which can be embodied by a computer-usable or computer-readable storage medium comprising computer-usable or computer-readable program instructions, "code" or a "computer program" embodied on said medium for use on or in connection with the instruction-executing system. Such a system can be a computer; a computer can be a data processing device comprising means for executing the computer program elements and/or the program in accordance with the invention. Within the context of this invention, a computer-usable or computer-readable medium can be any medium which can contain, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus, device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular constitute a guidance information device which includes means for outputting guidance information. The guidance information can for example be output to a user visually by a visual indicating means (for example, a monitor and/or a lamp) and/or acoustically by an acoustic indicating means (for example, a loudspeaker and/or digital speech output device) and/or tactilely by a tactile indicating means (for example, a vibrating element or vibration element incorporated into an instrument).

Within the framework of the invention, it is possible to combine individual features or a number of features of the embodiments, alternatives and examples described above with each other or to omit features which are not absolutely necessary from combinations of features.

BRIEF DESCRIPTION OF THE DRAWINGS

The present invention shall be explained in more detail on the basis of an example embodiment.

DETAILED DESCRIPTION

Figure 1:
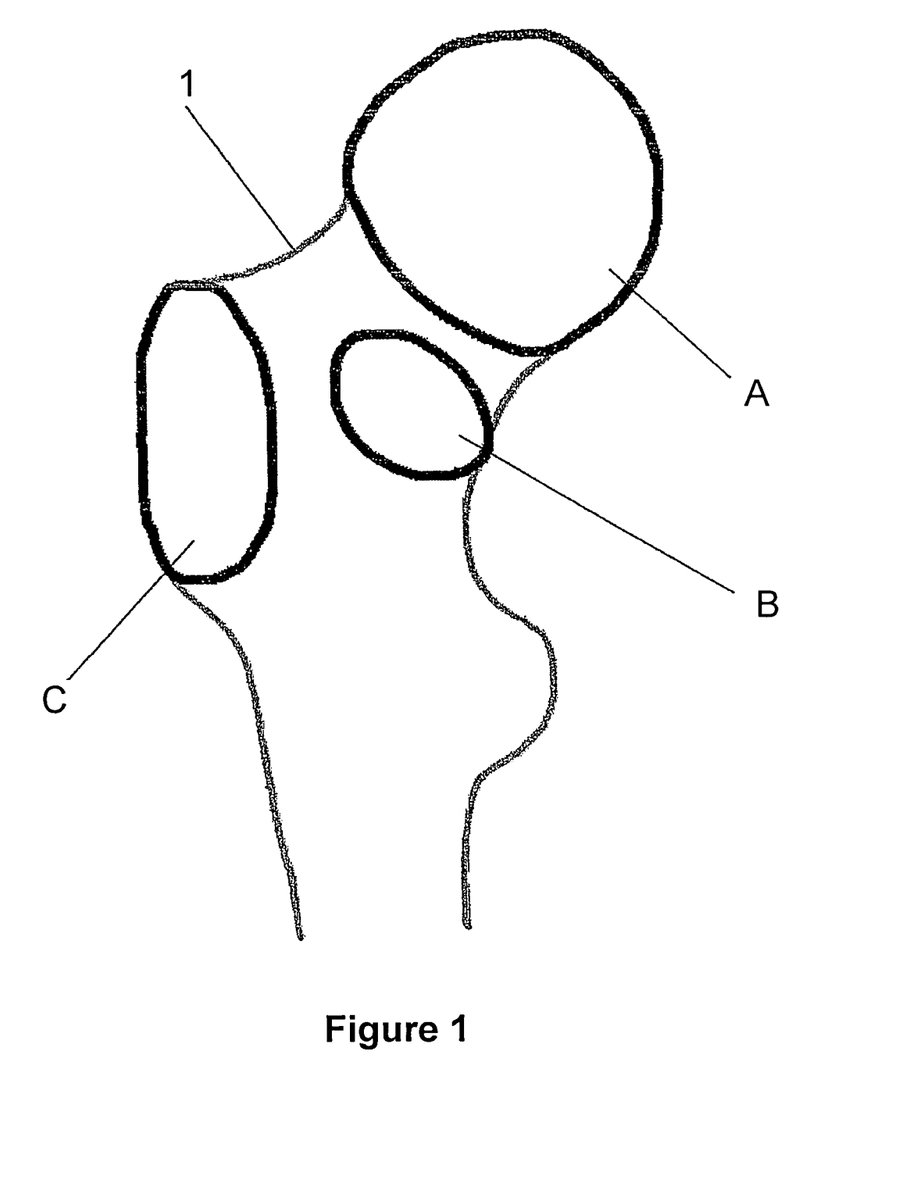
FIG. 1 shows a generic model comprising three marked regions.

FIG. 1 shows the contour of a two-dimensional projection of the statistical generic model 1 of a bone. The generic model 1 consists of a multitude of grid points (not shown), wherein the network of grid points simulates the average shape of an anatomical structure—in the present case, a femoral bone—in its initial state. The generic model 1 is altered with the aid of a morphing method, in order to reproduce an anatomical structure of a specific patient as precisely as possible. The morphing method uses measurement point data which represents scanned measurement points on the surface of the anatomical structure, wherein the arrangement of the measurement points is initially determined by means of the method in accordance with the invention for each region to be scanned.

To this end, three regions A, B and C of the generic model 1 are for example initially selected which are of particular interest for a medical application, for example in order to alter the bone or affix an implant in said regions. Since the surface characteristics of the bone in the regions corresponding to the three regions A, B and C can be variously complex, the corresponding regions of the bone are scanned at different levels of precision. The arrangement data which represents the arrangement of the measurement points are individually determined for each of the regions of the bones, i.e. in accordance with the required scanning precision.

Figure 2:
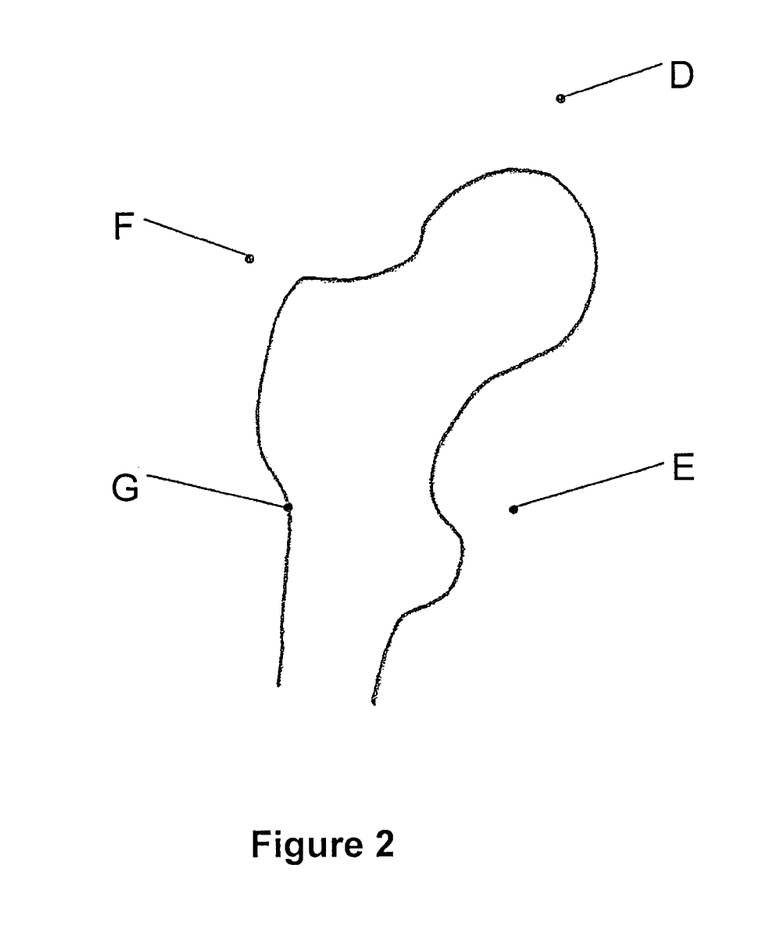
FIG. 2 shows the generic model and four landmarks.
Figure 3:
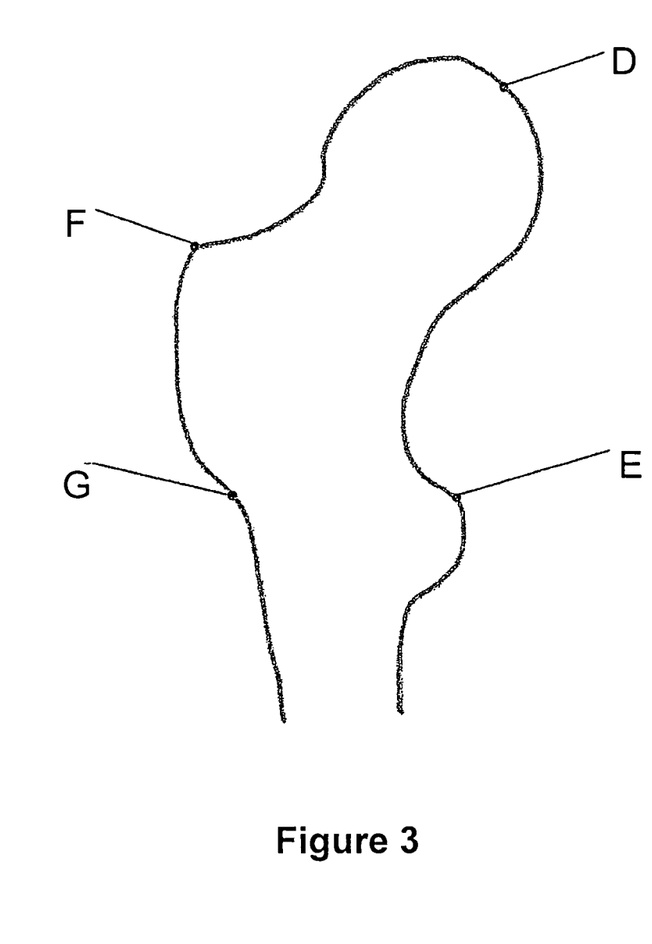
FIG. 3 shows the model, scaled onto the landmarks.

To this end, pre-registration is initially performed, wherein for example four landmarks D, E, F and G of the bone are scanned in order to generate pre-registration data which is then used by the method in accordance with the invention to determine the arrangement data. As can be seen from FIG. 2, these scanned landmarks do not necessarily match the corresponding landmarks of the model 1. The model 1 is therefore scaled and aligned in accordance with the method, such that the scanned landmarks D to G match the corresponding landmarks of the model 1 as closely as possible. This state is shown in FIG. 3. A spatial relationship between the model 1 and the landmarks D to G of the bone is simultaneously established in this step. This subsequently enables a scanned measurement point of the bone to be assigned to one or more grid points of the generic model 1.

Before the proposals for scanning the three regions of the bone are output, the arrangement—for each of the regions—of the measurement points proposed for scanning in this region are individually determined. The arrangement of the proposed measurement points includes the distance between the measurement points and thus the number of measurement points within the respective region. To this end, each of the three regions is assigned a complexity. The complexity of each region is derived from the model 1. Each grid point of the regions A, B and C of the generic model 1 is assigned a complexity, or the complexity is determined from the density of the grid points of the generic model 1 in the respective region. The complexity of a region of the bone corresponds to the complexity of the corresponding region of the generic model 1. Alternatively, the complexity of a region of the bone is obtained from image data which includes an image of the bone, for example in the form of an x-ray image or an MRT image.

Figure 4:
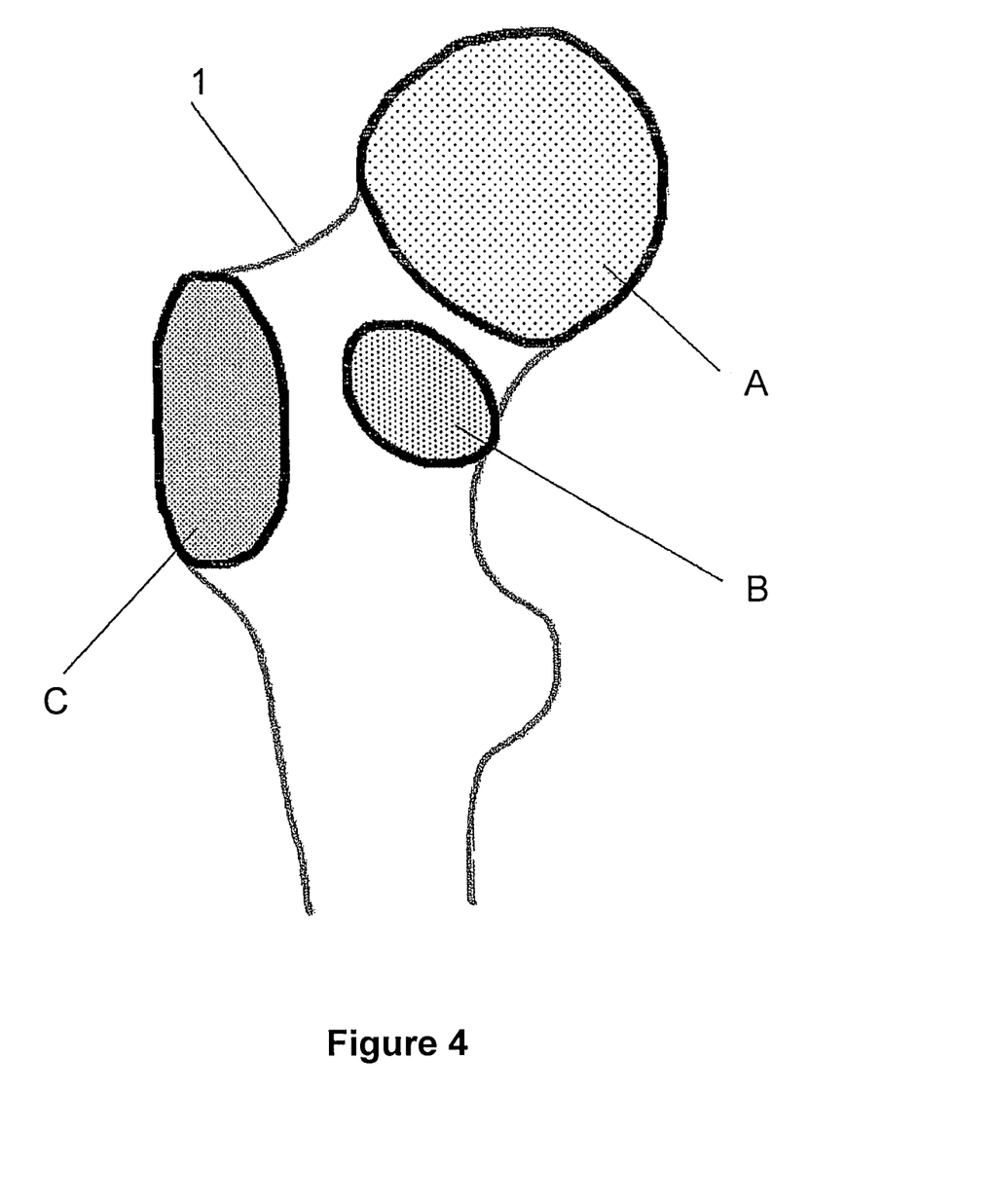
FIG. 4 shows the arrangements of the measurement points in the three regions.

In the present example, the region A exhibits a low complexity, which leads to a low density of measurement points in the corresponding region of the bone. The region B has a medium complexity, and the region C has a high complexity. Correspondingly, there is a medium density of measurement points in the region of the bone corresponding to the region B, and a high density of measurement points in the region of the bone corresponding to the region C. This is shown in FIG. 4 by the regions A, B and C which are filled-in at different densities.

Figure 5:
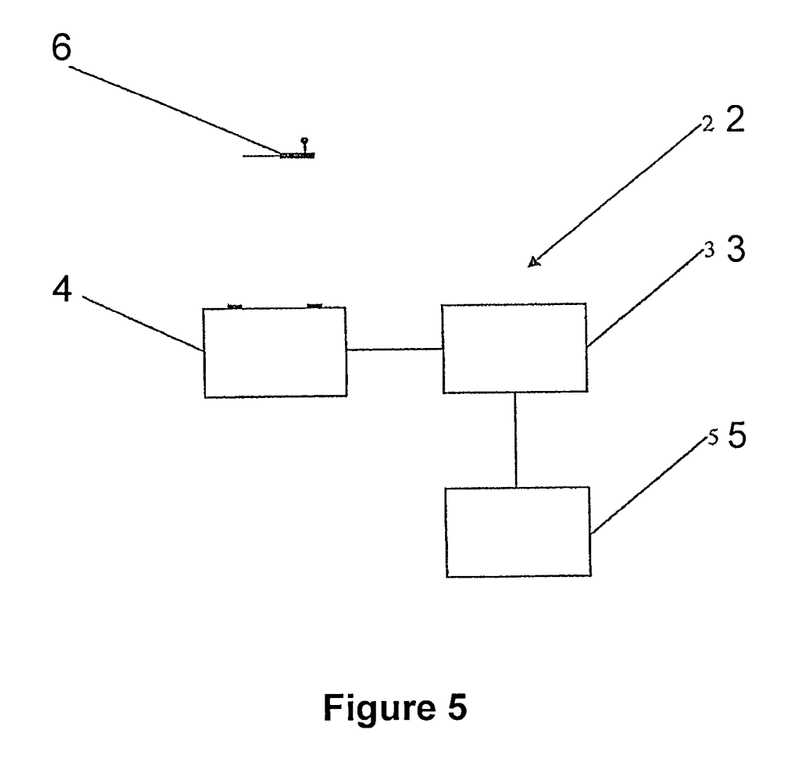
FIG. 5 shows a device in accordance with the invention.

FIG. 5 shows a device 2 in accordance with the invention for determining arrangement data which represents an arrangement of measurement points on an anatomical structure. The device comprises a computer 3 in which the generic model 1 of the bone is stored. The computer 3 is connected to a screen 4 and a 3D camera 5. The camera 5 serves to stereoscopically detect a pointer 6. The computer ascertains the position, i.e. the location and/or alignment, of the pointer 6 and its tip.

The landmarks D, E, F and G of the bone are scanned by means of the pointer 6 and provided to the computer 3 as landmark data. The computer 3 then calculates the arrangement data, i.e. the arrangement of the measurement points in the regions A, B and C, on the basis of the method described above.

By means of a scanning process, the three regions of the bone are for example scanned by means of the pointer 6 and in accordance with the arrangement of the measurement points in the respective region, and measurement point data is generated which is then used by a subsequent method to morph the generic model 1 onto the bone. A measurement point described by the measurement point data can be assigned to one of the three regions A to C on the basis of the pre-registration. The region of the bone to be scanned is preferably indicated to the operator performing the scan by the method or by the device 2. To this end, the generic model 1 is for example displayed on the screen 4 and the region to be scanned is optically highlighted on the screen 4. The operator is preferably also notified when a sufficient number of measurement points have been scanned in a region.

On the basis of the measurement point data which represents the scanned measurement points of the surface of the bone, the position of the grid points of the generic model 1 are varied such that the generic model 1 matches the surface of the bone as closely as possible. Methods for this step, which is referred to as morphing or matching, are part of the prior art and therefore known to the person skilled in the art. The morphing is for example likewise performed by the computer 3.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for determining arrangement data which represents an arrangement of measurement points on an anatomical structure of a patient according to which the anatomical structure is to be scanned, comprising:
    prior to scanning the anatomical structure, i) assigning a complexity to each of a plurality of different regions of the anatomical structure, and ii) individually determining the arrangement data for each of the plurality of different regions of the anatomical structure based on the complexity assigned to each respective region,
    wherein assigning the complexity includes determining regions of a generic model of the anatomical structure which correspond to the regions of the anatomical structure, and ascertaining the complexity of a region of the anatomical structure from the complexity of the corresponding region of the generic model.

2. The method according to claim 1, wherein the arrangement data includes the number of measurement points and/or the distance between the measurement points.

3. The method according to claim 1, wherein assigning the complexity includes assigning the complexity to at least one adjacent region.

4. The method according to claim 1 wherein
    determining regions of the generic model includes using a generic model that consists of grid points, each grid point assigned a complexity, and
    assigning the complexity to each of the plurality of different regions includes ascertaining the complexity of a region of the generic model from the complexity of the grid points in the respective region.

5. The method according to claim 1, wherein
    determining regions of the generic model includes using a generic model that includes grid points, and
    assigning the complexity includes ascertaining the complexity of a region of the generic model from the density of the grid points in the respective region.

6. The method according to claim 1, further comprising ascertaining the generic model by averaging scanning values of a multitude of homogenous surveyed structures,
    wherein assigning the complexity includes ascertaining the complexity of a region of the generic model on the basis of the variance of the scanning values, averaged with respect to the generic model, of the structures in the respective region.

7. The method according to claim 1, further comprising adapting the generic model to the anatomical structure of the patient on the basis of pre-registration data which represents landmarks of the anatomical structure of the patient,
    wherein assigning the complexity includes ascertaining the complexity of a region of the anatomical structure from the complexity of the corresponding region of the adapted generic model.

8. The method according to claim 1, wherein individually determining arrangement data includes determining the arrangement data of a region on the basis of an image of the anatomical structure.

9. A method for morphing a generic model of an anatomical structure onto an anatomical structure of a patient on the basis of measurement point data which represents the anatomical structure at measurement points, wherein arrangement data which represents the arrangement of the measurement points is determined on the basis of a method according to claim 1.

10. The method according to claim 9, wherein the generic model is adapted to the arrangement data.

11. A non-transitory computer readable medium comprising computer executable instructions adapted to perform the method in accordance with claim 1.

12. A device for determining arrangement data which represents an arrangement of measurement points on an anatomical structure, said device comprising a computer which is designed to perform the method according to claim 1.

13. The method according to claim 8, wherein determining the arrangement data of a region on the basis of an image includes using an x-ray image or a CT recording as the image.

14. The method according to claim 1, wherein individually determining the arrangement data comprises:
    identifying regions on the anatomical structure;
    classifying the identified regions based on the level of complexity of the respective regions; and
    individually determining the arrangement data for different ones of the regions based on the level of complexity of the respective region or at least one adjacent region.

15. The method according to claim 14, wherein classifying the identified regions of interest based on the level of complexity of the respective regions of interest includes using a number of grid points of a generic model that define an average shape of the anatomical structure to assign the level of complexity to the respective region of interest.

16. The method according to claim 1, wherein assigning the complexity includes comparing an image of the anatomical region with a corresponding image of a generic model, and determining the complexity based on a deviation between two images of the region.

17. The method according to claim 1, wherein prior to scanning the anatomical structure includes prior to scanning the structure with a device that obtains three-dimensional spatial coordinates of the structure.

* * * * *